United States Patent [19]
Colon et al.

[11] Patent Number: 5,402,799
[45] Date of Patent: Apr. 4, 1995

[54] GUIDEWIRE HAVING FLEXIBLE FLOPPY TIP

[75] Inventors: Michael Colon, Waltham, Mass.; Philip P. Corso, Jr., Davie; Fernando M. Viera, Hialeah, both of Fla.

[73] Assignee: Cordis Corporation, Miami Lakes, Fla.

[21] Appl. No.: 84,548

[22] Filed: Jun. 29, 1993

[51] Int. Cl.⁶ .............................................. A61B 5/00
[52] U.S. Cl. .................................................... 128/772
[58] Field of Search .................. 128/657, 658, 772; 604/95, 280–283

[56] References Cited

U.S. PATENT DOCUMENTS

| | | | |
|---|---|---|---|
| 3,528,406 | 9/1970 | Jeckel et al. | 128/2.05 |
| 3,753,700 | 8/1973 | Harrison et al. | 75/175.5 |
| 3,789,841 | 2/1974 | Antoshkiw | 128/2.05 R |
| 3,906,938 | 9/1975 | Fleischhacker | 128/2 M |
| 4,283,233 | 8/1981 | Goldstein et al. | 148/11.5 R |
| 4,503,569 | 3/1985 | Dotter | 3/1.4 |
| 4,538,622 | 9/1985 | Samson et al. | 128/772 |
| 4,619,274 | 10/1986 | Morrison | 128/772 |
| 4,665,906 | 5/1987 | Jervis | 128/92 YN |
| 4,721,117 | 1/1988 | Mar et al. | 128/772 |
| 4,763,647 | 8/1988 | Gambale | 128/657 |
| 4,813,434 | 3/1989 | Buchbinder et al. | 128/772 |
| 4,832,444 | 5/1989 | Takahashi et al. | 350/96.26 |
| 4,846,186 | 7/1989 | Box et al. | 128/657 |
| 4,925,445 | 5/1990 | Sakamoto et al. | 604/95 |
| 4,969,890 | 11/1990 | Sugita et al. | 606/192 |
| 4,984,581 | 1/1991 | Stice | 128/772 |
| 5,069,226 | 12/1991 | Yamauchi et al. | 128/772 |

FOREIGN PATENT DOCUMENTS 141006  5/1985  European Pat. Off.
376132  7/1990  European Pat. Off.

OTHER PUBLICATIONS

Suzuki, Yuichi, "Shape Memory and Super-Elasticity Effects in NiTi Alloys", The Furukawa Electric Co., Ltd., Tokyo, vol. 30, No. 4, May 1993.

*Primary Examiner*—Max Hindenburg
*Attorney, Agent, or Firm*—Lockwood, Alex, Fitzgibbon & Cummings

[57] ABSTRACT

A guidewire is provided for use with medical devices such as catheters. The guidewire has a structure which is particularly suitable for use as a micro-guidewire which is small enough for use even within the cerebral vascular system. The guidewire includes a unitary core wire of nickel and titanium alloy, which unitary core wire has a distal tip portion including a ribbon tip. A coil is positioned generally along the outside surface of the distal tip portion, including the ribbon tip. The distal tip portion of the device exhibits super-elasticity properties by which the tip is easily bent and rebent without kinking.

13 Claims, 1 Drawing Sheet

U.S. Patent  Apr. 4, 1995  5,402,799
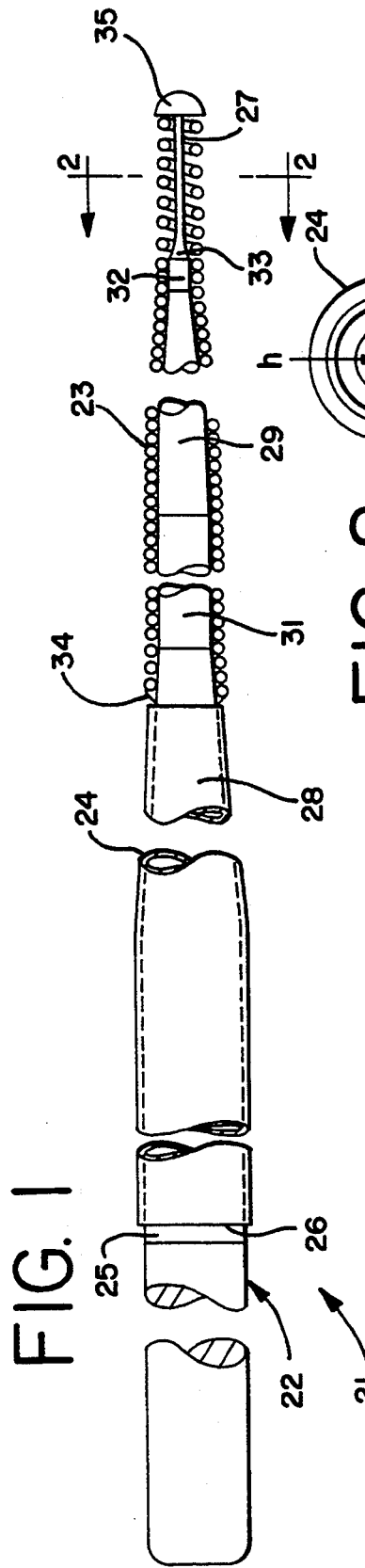
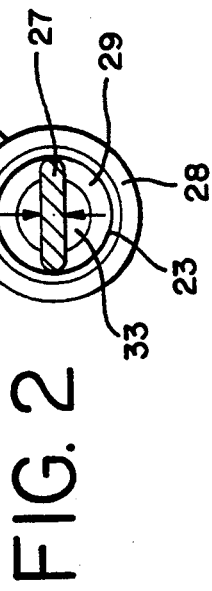
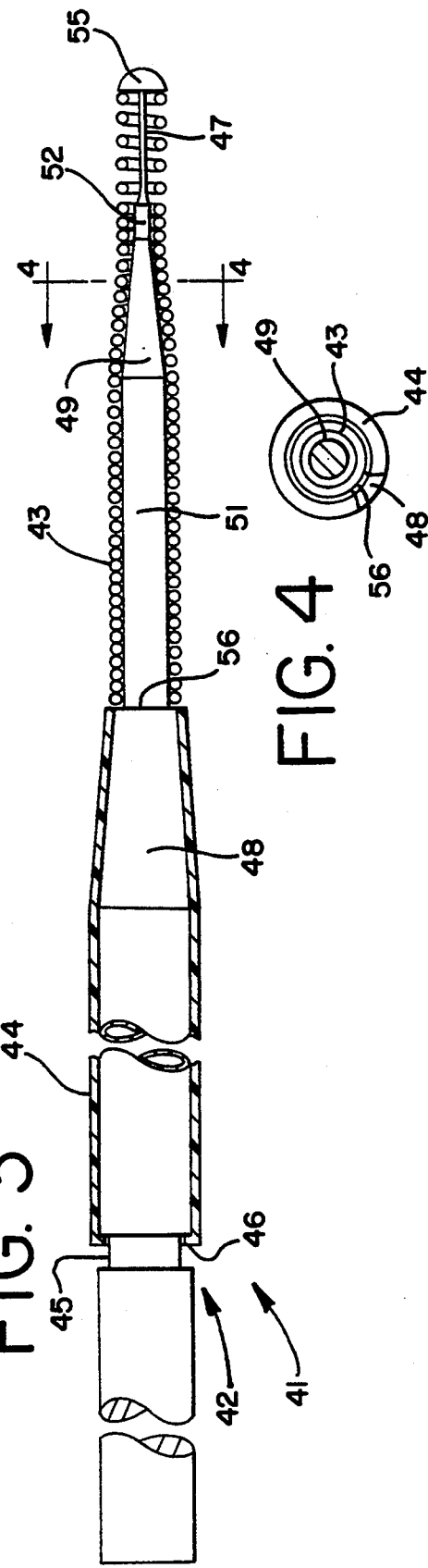
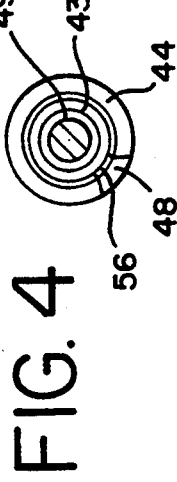

GUIDEWIRE HAVING FLEXIBLE FLOPPY TIP

DESCRIPTION

Background and Description of the Invention

The present invention generally relates to guidewires for use with medical catheters, which guidewires are particularly suitable for guiding catheters which have especially small diameters. The guidewire is exceptionally maneuverable and flexible while still exhibiting adequate torque for effective transluminal insertion. The distal tip end of the guidewire has a flattened ribbon tip and is made of nickel and titanium alloy. A metallic coil is co-axially positioned over the distal tip portion of the guidewire, including its ribbon tip. The ribbon tip and the coil are secured together such as by welding at the very distal tip end of the guidewire. The thus formed tip exhibits an exceptional ability to be bent to a desired configuration prior to insertion and rebent as desired without kinking, while at least the length of the guidewire having the ribbon tip presents a floppy characteristic which facilitates the ability of the guidewire to seek out and pass through bends in body passageways, such as branching blood vessels.

Guidewires have long been used in many medical procedures. Generally speaking, a guidewire is the initial member inserted into a body cavity during many transluminal procedures. A guidewire is an elongated fine wire that is intended to readily pass through body passageways and to a location at which a medical procedure or treatment is to take place. Thereafter, a catheter is slid over the thus inserted guidewire, with the catheter following the pathway defined by the guidewire. Proposals for enhancing the flexibility of the distal tip portions of guidewires include providing a flattened tip guidewire within a guidewire coil, the flattened tip and coil being secured together at the remote distal tip end. Examples in this regard include Box et al. U.S. Pat. No. 4,846,186 and Mar et al. U.S. Pat. No. 4,721,117. In these types of approaches, the elongated core wire of the guidewire is made of stainless steel which provides good torque properties for steerability purposes. However, tip flexibility is limited by the inability of the stainless steel to bend easily and to be rebent without developing kinks along the bend.

Medical devices also have been proposed or provided which utilize thermal change properties of so-called shape memory alloys. Guidewires made of such materials exhibit an original heat stable configuration, or austenite condition, and a heat unstable configuration, or martensite condition. Such shape memory alloys are characterized by being able to move from the austentic state to the martensitic state by lowering the temperature of the alloy. Transformation from martensitic state to the austentic state is effected by raising the temperature of the alloy. Alloys of this type are typically characterized by austentic temperature values. The temperature at which the alloy begins to revert beck to the austentic state is referred to as $A_s$, while the temperature at which this reversion is complete is referred to as $A_f$. In the case of a device such as a guidewire, these properties can be used to have an increase in temperature imparted to the guidewire by the warm-blooded body into which the guidewire is inserted effect a shape transformation which is believed to be desirable for guidewire manipulation and placement. Alloys exhibiting these shape memory properties are discussed in Jervis U.S. Pat. No. 4,665,906, Sakamoto et al. U.S. Pat. No. 4,925,445 and Yamaychi et al. U.S. Pat. No. 5,069,226.

It has been found that guidewires in accordance with the present invention provide a combination of properties including good torsional properties for steerability, exceptional tip flexibility, super-elasticity, and the ability of the tip to be bent or shaped by the physician prior to insertion, including the ability to be rebent without kinking. In summary, the present invention achieves these objectives and provides advantageous results along these lines by combining the features of a core wire made of a nickel and titanium alloy having austentic properties that are selected so they do not effect a shape change during normal temperatures to which the guidewire is subjected during use. This feature is combined with providing the core wire with a ribbon tip and a co-axial flexible coil that substantially surrounds the entirety of the ribbon tip and a substantial portion of the remainder of the distal tip portion of the guidewire.

It is a general object of the present invention to provide an improved medical guidewire.

Another object of this invention is to provide an improved guidewire which is suitable for use as a micro-guidewire within extremely fine vessels, including cerebral vessels, such as in the cerebral vascular system.

Another object of the present invention is to provide an improved medical catheter having an exceptionally flexible and floppy tip that readily accesses branched and angled vessel passageways, even those requiring the tip and catheter to bend through an angle of 90 degrees or greater.

Another object of this invention is to provide an improved catheter guidewire which includes features to assist in pushing and/or steering of the guidewire, including the use of tapers along the length of the guidewire, particularly along its tip portion.

Another object of this invention is to provide an improved catheter guidewire having a core wire made of an alloy known to have shape memory properties, but at austentic temperatures other than those encountered during guidewire use, such that the core wire does not undergo a temperature-induced shape change or reversion during use but does exhibit super-elasticity properties at in-use temperatures.

Another object of this invention is to provide an improved guidewire having a tip portion exhibiting superelastic characteristics and freedom from kinking under in-use conditions.

These and other objects, features and advantages of this invention will be clearly understood through a consideration of the following detailed description.

BRIEF DESCRIPTION OF THE DRAWINGS

The invention will be further elucidated in the following description with reference to the drawings in which:

FIG. 1 is a longitudinal view, partially broken away, with the coil being shown in cross-section, of a guidewire in accordance with the present invention;

FIG. 2 is a transverse cross-sectional view along the line 2—2 of FIG. 1;

FIG. 3 is a view, partially in longitudinal cross-section and partially in elevation, of another embodiment of the guidewire in accordance with this invention; and FIG. 4 is a transverse cross-sectional view along the line 4—4 of FIG. 3.

DESCRIPTION OF THE PARTICULAR EMBODIMENTS

A guidewire, generally designated as 21, is illustrated in FIG. 1. Included is an elongated core wire, generally designated as 22 and a substantially helical coil 23 secured thereto. In the preferred embodiment, the entire elongated core wire 22 is a unitary, one-piece member which includes the various features thereof as discussed herein.

It is also preferred that a portion of the elongated core wire 22 is covered with a polymeric sleeve 24 as illustrated. Typically, the sleeve 24 is made of a lubricious material and is provided in order to reduce potential trauma during insertion into the patient. Preferably, the core wire 22 includes an undercut 25 at the proximal edge of the polymeric sleeve 24. The preferred polymeric sleeve 24 will undergo shrinking during application onto the core wire 22, with the result that the proximal edge 26 of the polymeric sleeve 24 wraps around an inside wall of the undercut 25 in order to provide a secure and smooth connection between the polymeric sleeve and the core wire.

With more particular reference to the core wire 22, the proximal portion thereof is of a substantially uniform diameter. The core wire tapers down in a distal direction. A ribbon tip defines the remote distal tip portion of the core wire 22. The ribbon tip 27 is formed by flattening the desired length of the proximal end portion of the core wire by a procedure in which force is applied to the core wire at this location until it is flattened to the cross-section generally shown in FIG. 2. The cross-sectional height is substantially less than the cross-sectional width. In addition, as is evident from FIG. 1 and FIG. 2, the cross-sectional height "h" is less than the cross-sectional height or diameter of the remainder of the core wire. A procedure by which the ribbon tip 27 can be formed is generally described in U.S. Pat. No. 4,846,186, the disclosure thereof being incorporated by reference hereinto. It will be appreciated that in the illustrated embodiments, the ribbon tip 27 is formed from and is an integral component of the core wire itself.

Proximal of the ribbon tip 27, but generally along the distal portion of the core wire, there is located a tapering portion. This tapering portion provides two functions. First, it provides a gradual transition or reduction in diameter size in order to thereby increase the flexibility of this portion of the core wire. Secondly, the generally conical or frusto-conical portions of this tapering portion enhance the torsional control or pushability and steerability of this portion of the device, which is particularly important because the device incorporates a core wire which is made of a material other than heretofore customarily used materials such as stainless steel.

FIGS. 1 and 2 show this gradual transition length to be a substantially totally tapered length, made up of a series of tapered portions located end-to-end with respect to each other. Included is a first or proximal tapered portion 28, a second, or intermediate tapered portion 31, and a third, or distal tapered portion 29. These various tapered portions are preferably formed by centerless grinding of the elongated core wire in order to form the various portions of the tapering distal length of the device. A unidiametric portion 32 can be provided immediately proximal of a final distal tapered portion 33.

In the embodiment illustrated in FIGS. 1 and 2, the helical coil 23 extends from the tip and proximally to a location along the first or proximal tapered portion 28. In this manner, the diameter of the coil as defined by its contact with the core wire tapered portion 28 is not greater than the maximum outer diameter of the device, thereby avoiding having the helical coil present a profile greater than the rest of the device. As specifically illustrated in FIG. 1, the proximal end of the helical coil generally coincides with the distal end of the polymeric sleeve 24, with the result that the polymeric sleeve defines an indent for contributing to a smoother transition between the proximal end of the helical coil 23 and the rest of the device than if the indent were not provided. As illustrated, a cement or weld 34 can be included to both secure the proximal end of the helical coil and also eliminate any abrupt shoulder that might remain at the interface between the proximal end of the helical coil and the rest of the device. A typical material in this regard can be an epoxy adhesive or the like.

With respect to the distal end of the helical coil 23, this distal end as well as the distal end of the ribbon tip 27 terminate in a generally smooth or atraumatic tip bond 35. By this arrangement, the helical coil and the ribbon tip are secured together in a manner which provides a generally atraumatic leading tip for the catheter device.

It will be observed that, with the device thus assembled, the distal end portion of the core wire, and especially the ribbon tip 27 thereof, will be especially flexible. The flexibility at this portion of the device is further enhanced by increasing the spacing between adjacent turns of the helical coil 23 as illustrated. In addition, it will be observed that there is radial spacing between the inside surface of the coil and at least the height of the ribbon tip, thereby further enhancing flexibility.

Especially important to the flexibility and malleability of the guidewires in accordance with the present invention is the material out of which the core wire is made, which is an alloy including nickel and titanium. These are generally categorized as Nitinol alloys. In an important aspect of this invention, these nickel and titanium-containing alloys are selected to have austenic properties that do not effect a shape change during normal temperatures to which the guidewire is subjected during use. Alloys of this type exhibit super-elasticity. They are particularly useful for these types of guidewires because they can be readily bent by the physician prior to insertion in order to impart a desired end shape to the guidewire, such as a J-shape. Once bent, the tip portion in accordance with the invention can be straightened and bent again without the development of any noticeable kinking at the bending locations. Core wires made of stainless steel, for example, exhibit kinking when bent and straightened to the extent that it typically is not possible to fully eliminate a bend before the bending to a more desirable shape. This can be important, for example, when the physician makes an initial bend that is not to his or her satisfaction. With a guidewire in accordance with the present invention, the physician is able to make an initial bend and inspect it. If not satisfactory, the tip is readily bent back to its original configuration (such as a straight configuration). Thereafter, the physician can proceed with a second bend until the desired tip configuration is prepared.

It has been found that the properties characteristic of this invention are achieved when using core wires as discussed herein made with alloys of nickel and titanium which exhibit an austenitic temperature greater than about 10° C. and not greater than about 20° C. Such devices exhibit the super-elasticity which is characteristic of the invention and do not undergo temperature-induced shape changes normally associated with shape memory alloys at the temperatures to which the guidewire is subjected during normal use, including warm-blooded body temperatures and room temperature. Once the tip portion in accordance with the invention is selected and/or bent by the physician, that shape is not modified by temperature changes within normal use temperature ranges. In addition, it has been found that, if the alloy has an $A_f$ temperature above about 20° C., this super-elastic characteristic which permits bending without kinking will be diminished. The guidewires made in accordance with the present invention are very elastic and exhibit superior elasticity properties such as bending freedom and kink resistance. Furthermore, because of the combination of features of the present guidewires, they are not only flexible, but they exhibit very good steerability and torque extremely well during insertion.

The present guidewires, particularly due to the core wire alloy, can be used to access multiple vascular tracks. If the guidewire is bent or positioned for movement through a path within a vessel, the bend or position can be modified, and the guidewire can be put into another path requiring a different bend. Once a different core wire, such as the typically used stainless steel core wire, takes a set, it cannot be put into another path because it kinks and does not return to its original shape.

Super-elasticity and micro-sizing aspects of the guidewires of this invention make them especially suitable for delicate applications within small and highly branched vessels, even such as those within the cerebral vascular system which has very tortuous and typically very narrow passageways. Micro-guidewires made according to present invention are able to operate within the cerebral vascular system and are able to access locations therein which cannot be accessed by other guidewires.

FIGS. 3 and 4 illustrate another embodiment of the present invention. The primary difference between the illustrated embodiments is the manner in which the gradual transition from core wire body to ribbon tip is accomplished. Guidewire 41 includes elongated coil wire 42 having distally located helical coil 43 positioned over a distal portion thereof. Polymeric sleeve 44 spans the length of the guidewire between the proximal end of the helical coil 43 and undercut 45, within which proximal edge 46 of the polymeric sleeve 44 rests.

The gradual transition area begins proximally with first or proximal tapered portion 48, followed by unidiametric portion 51 and a second or distal tapered portion 49, followed by a transition to ribbon tip 47, the illustrated transition being a unidiametric portion 52. The guidewire 41 terminates distally with tip bond 55. In this arrangement, a discernable shoulder or step 56 is positioned between the unidiametric portion 51 and the tapered portion 48 in order to fully and directly accommodate the thickness of the helical coil 43. This provides a smoother profile at the transition between the helical coil and the rest of the guidewire, thereby improving the atraumatic properties of the guidewire against vessel walls. This shoulder or step 56 also increases the flexibility and somewhat decreases the torqueability of the guidewire. It has been found that, in general, a unidirectional length provides less torqueability and greater flexibility at this location, when compared with, for example, multiple tapering arrangements not having a shoulder or step as illustrated in the FIG. 1 embodiment by portions 28, 31 and 29 when compared with the structure comprised of tapered portion 48, step 56, unidiametric portion 51, and tapered portion 49. Elongated core wire 22, 42 is made of an alloy including nickel and titanium in an approximate 50:50 mixture and having a raw state temperature typically greater than about 10° C. and not greater than about 20° C. as the $A_f$ temperature range. The tensile strength of the core wire is a minimum of 150 KPSI, preferably at least about 180 KPSI. A typical core wire has a diameter of 0.014 inch along its proximal length, and the polymeric sleeve has a thickness of approximately 0.001 inch such that a typical coated core wire has a diameter of 0.016 inch. These guidewire sizes can range between about 0.008 inch and about 0.025 inch, depending upon the intended end use, with the smaller sizes being of a type suitable for use within the cerebral vascular system.

A preferred blend of the alloy contains between about 49.5 and about 50.5 weight percent, plus or minus about 1 weight percent of nickel and of titanium. The preferred material is 99% pure nickel and titanium. Preferably, other than trace impurities, the core wire usually will contain no additional metals such as iron, copper or aluminum.

The preferred ribbon tip 27, 47 is preferably made by flattening the distal end portion of the core wire which had been centerless ground to a diameter of about 0.0025 inch to about 0.0030 inch. After flattening, the height "h" will typically be about 0.0012 inch. Its other transverse cross-sectional dimension, or width, will typically be approximately three times its height, generally between about 0.0030 and about 0.0045 inch. The exact dimensions of the ribbon tip will vary somewhat depending upon the overall sizing of the guidewire. A typical ribbon tip will have a length of about 1 inch to about 3 inches.

Typical dimensions for the total tapering embodiment illustrated in FIG. 1 are as follows. The total guidewire will have a length of on the order of 70 inches, with the gradual diameter reduction distal portion having a length of about 12 to 16 inches in a typical example of this type of device. The first or proximal tapered portion 28 has a length of about 3.5 inches and, for a core wire having a 0.014 inch diameter, tapers down to a diameter of about 0.007 inch. The second or intermediate tapered portion 31 has a typical length of about 6.5 inches and gradually tapers down to about 0.004 inch in diameter. The third or distal tapered portion 29 has a typical length of about 3.2 inch and tapers down to about 0.0025 inch in diameter. In an example of the embodiment shown in FIG. 3, the tapering portions have similar dimensions to like portions in the above example of the FIG. 1 embodiment, except the degree of taper for the first or proximal tapered portion 48 is somewhat less, tapering from about 0.014 inch to about 0.011 inch in diameter. The unidiametric portion 51 in this example has a diameter of about 0.007 inch. Also, the degree of taper of the second or distal tapered portion 49 is somewhat steeper than in the FIG. 1 illustration, this portion tapering from about 0.007 inch to about 0.0025 inch. In effect, the FIG. 3 embodiment replaces one of the tapered portions of the FIG. 1 embodiment with a unidiametric portion in order to provide the desirable step or shoulder as illustrated.

With further reference to the helical coil 23, 43, it is preferably made of a platinum and tungsten alloy comprised of approximately 92 weight percent platinum and approximately 8 weight percent tungsten. Adjacent turns of the helical coil will typically be in general engagement with each other such that there is no substantial spacing therebetween throughout much of the length of the coil. It is preferred that the distal end portion of the coil, typically that portion which generally envelopes the ribbon tip 27, 47, provides for spacing between the adjacent turns. Typical spacing in this regard will be not greater than about the diameter of the wire making up the helical coil. This distal portion having spaced-apart turns will have a length on the order of about 3.5 inches. It is preferred, as illustrated, that the distal portion of the helical coil be radially spaced away from engagement with the distal end portion of the core wire, particularly its ribbon tip.

It will understood that the embodiments of the present invention which have been described are illustrative of some of the applications of the principles of the present invention. Various modifications may be made by those skilled in the art without departing from the true spirit and scope of the invention.

We claim:

1. A guidewire for use with a medical device catheter, comprising:

a longitudinally extending core wire having a distal tip portion and an elongated body portion proximal of said distal tip portion, said longitudinally extending core wire being readily bendable from an original configuration to another configuration without kinking, including returning to the original configuration without kinking, said core wire being an alloy including nickel and titanium as the principal components, said alloy having austentic properties selected to substantially preclude temperature-induced shape changes during normal use temperatures, said properties including having an $A_f$ temperature, at which reversion to an austentic state is complete, of greater than about 10° C. and not greater than about 20° C.;

a ribbon tip at the distal end of said distal tip portion, said ribbon tip being generally rectangular in transverse cross-section to define a ribbon tip width and a ribbon tip height, said ribbon tip height being less than said ribbon tip width and being the smallest transverse cross-sectional dimension along the distal tip portion of the longitudinally extending core wire; and a coil substantially coaxial with said distal tip portion, said coil extending from said ribbon tip and in a proximal direction along said distal tip portion, said coil substantially surrounding said ribbon tip, said ribbon tip and said coil being secured together.

2. The guidewire in accordance with claim 1, wherein said normal use temperatures include warm-blooded body temperature and room temperature.

3. The guidewire in accordance with claim 1, wherein said longitudinally extending core wire is a one-piece component formed from a single elongated wire and including the ribbon tip.

4. The guidewire in accordance with claim 1, wherein said distal tip portion of the longitudinally extending core wire is composed of an alloy that is substantially exclusively nickel and titanium in substantially equal weight proportions.

5. The guidewire in accordance with claim 4, wherein the weight percent of nickel is between about 49.5 and about 50.5 weight percent, and the weight percent of titanium is between about 49.5 and about 50.5 weight percent, based upon the total weight percent of the alloy.

6. The guidewire in accordance with claim 1, wherein the distal tip portion of the longitudinally extending core wire exhibits super-elasticity properties.

7. The guidewire in accordance with claim 1, wherein said coil is radially spaced away from said ribbon tip at the location of said ribbon tip height, and individual adjacent turns of the coil are spaced from each other in the longitudinal direction of the guidewire along a length including the length of the ribbon tip.

8. The guidewire in accordance with claim 1, wherein said ribbon tip width is at least about 3 times as great as said ribbon tip height.

9. The guidewire in accordance with claim 1, wherein said distal tip portion includes a plurality of tapered portions including an intermediate tapered portion positioned between a proximal tapered portion and a distal tapered portion, with a distal end of the proximal tapered portion coinciding with a proximal end of the intermediate tapered portion and a distal end of the intermediate tapered portion coinciding with a proximal end of the distal tapered portion.

10. The guidewire in accordance with claim 1, wherein said distal tip portion includes an isodiametric portion positioned between a proximal tapered portion and a distal tapered portion, a shoulder defined at a distal end of the proximal tapered portion and a proximal end of the unidiametric portion, said coil extends substantially to said shoulder, and said coil has an outer diameter equal to or less than a maximum diameter of said shoulder.

11. The guidewire in accordance with claim 1, wherein said coil is a helical coil of an alloy of platinum and tungsten.

12. The guidewire in accordance with claim 1, further including a polymeric sleeve generally along the length of the elongated body portion of the core wire, said polymeric sleeve extending generally from the proximal end of the coil to an undercut having a diameter less than that of the core wire at a location adjacent the undercut, and a proximal end of the polymeric sleeve is positioned within the undercut.

13. The guidewire in accordance with claim 1, wherein said guidewire is a micro-guidewire for use within a human cerebral vascular system, and said distal tip portion has a flexible, floppy tip.

* * * * *